United States Patent [19]
Thompson

[11] Patent Number: 5,233,984
[45] Date of Patent: Aug. 10, 1993

[54] IMPLANTABLE MULTI-AXIS POSITION AND ACTIVITY SENSOR

[75] Inventor: David L. Thompson, Fridley, Minn.

[73] Assignee: Medtronic, Inc., Minneapolis, Minn.

[21] Appl. No.: 677,699

[22] Filed: Mar. 29, 1991

[51] Int. Cl.⁵ .......................................... A61N 1/365
[52] U.S. Cl. .................................. 607/18; 128/782; 33/377; 607/19
[58] Field of Search ............ 128/419 P, 419 PG, 782, 128/419 D; 73/516 LM, 865.4; 33/366, 377

[56] References Cited

U.S. PATENT DOCUMENTS

| | | | |
|---|---|---|---|
| 3,163,856 | 12/1964 | Kirby | 128/782 |
| 3,442,023 | 5/1969 | Remington et al. | 33/366 |
| 3,487,303 | 12/1969 | Remington | 33/366 |
| 3,992,951 | 11/1976 | Erspamer et al. | 73/516 LM |
| 4,167,818 | 9/1979 | Cantarella et al. | 33/366 |
| 4,428,378 | 1/1984 | Anderson et al. | 128/419 PG |
| 4,771,780 | 9/1988 | Sholder | 128/419 PG |
| 4,811,491 | 3/1989 | Phillips et al. | 33/366 |
| 4,846,195 | 7/1989 | Alt | 128/419 PG |
| 4,869,251 | 9/1989 | Lekholm et al. | 128/419 PG |
| 4,896,068 | 1/1990 | Nilsson | 310/329 |
| 4,937,518 | 6/1990 | Donati et al. | 33/366 |
| 5,010,893 | 4/1991 | Sholder | 128/419 PG |
| 5,025,791 | 6/1991 | Niwa | 128/670 |
| 5,031,614 | 7/1991 | Alt | 128/419 PG |
| 5,031,618 | 7/1991 | Mullett | 128/421 |
| 5,044,365 | 9/1991 | Webb et al. | 128/419 PG |
| 5,052,388 | 10/1991 | Sivula et al. | 128/419 PG |

FOREIGN PATENT DOCUMENTS

| | | | |
|---|---|---|---|
| 0171961 | 2/1986 | European Pat. Off. | 33/377 |
| 0383732 | 8/1990 | European Pat. Off. | 128/782 |
| 1306567 | 4/1987 | U.S.S.R. | 128/782 |
| 2032110 | 4/1980 | United Kingdom | 33/366 |

OTHER PUBLICATIONS

Kenny et al., "Head-Up Tilt: A Useful Test for Investigating Unexplained Syncope", Lancet, Jun. 14, 1986.

Primary Examiner—Kyle L. Howell
Assistant Examiner—Kennedy J. Schaetzle
Attorney, Agent, or Firm—Harold R. Patton; Gregory P. Gadson

[57] ABSTRACT

A multi-axis, multi-purpose sensor for use with implantable medical devices, and for simultaneously detecting the patient's posture and activity level. The sensor includes a hermetically sealed, fluid-tight, bio-compatible housing. The housing is formed of a plurality of adjacently secured sides, and a plurality of side electrodes coupled to the sides. A central electrode is disposed at the geometric center of symmetry of the housing, to allow measurement of voltage changes between the central electrode and the side electrodes. A non-toxic electrically conductive electrolyte fills about half the housing, and immerses part of the central electrode and the side electrodes. The sensor further includes a low frequency bandpass filter for passing low frequency signals indicative of the patient's posture, and a high frequency bandpass filter for passing high frequency signals indicative of the patient's activity.

10 Claims, 3 Drawing Sheets

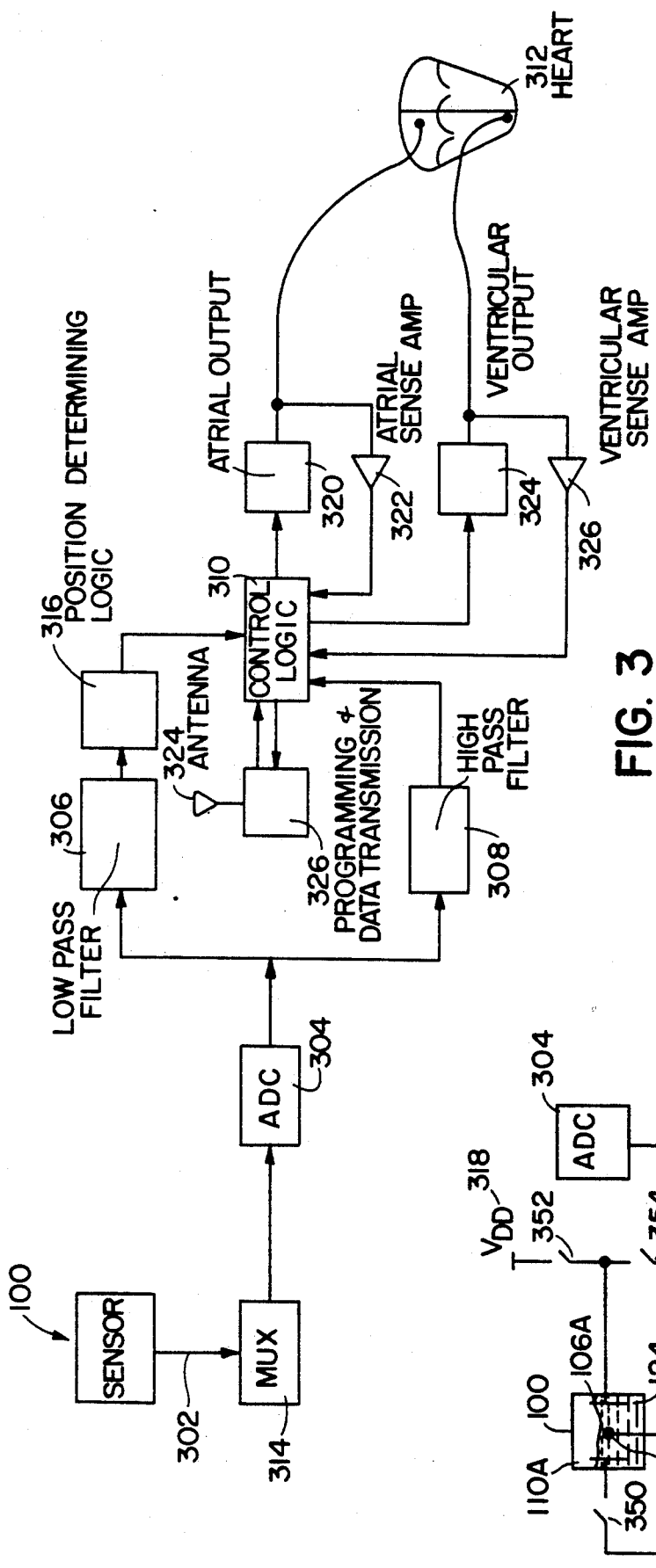

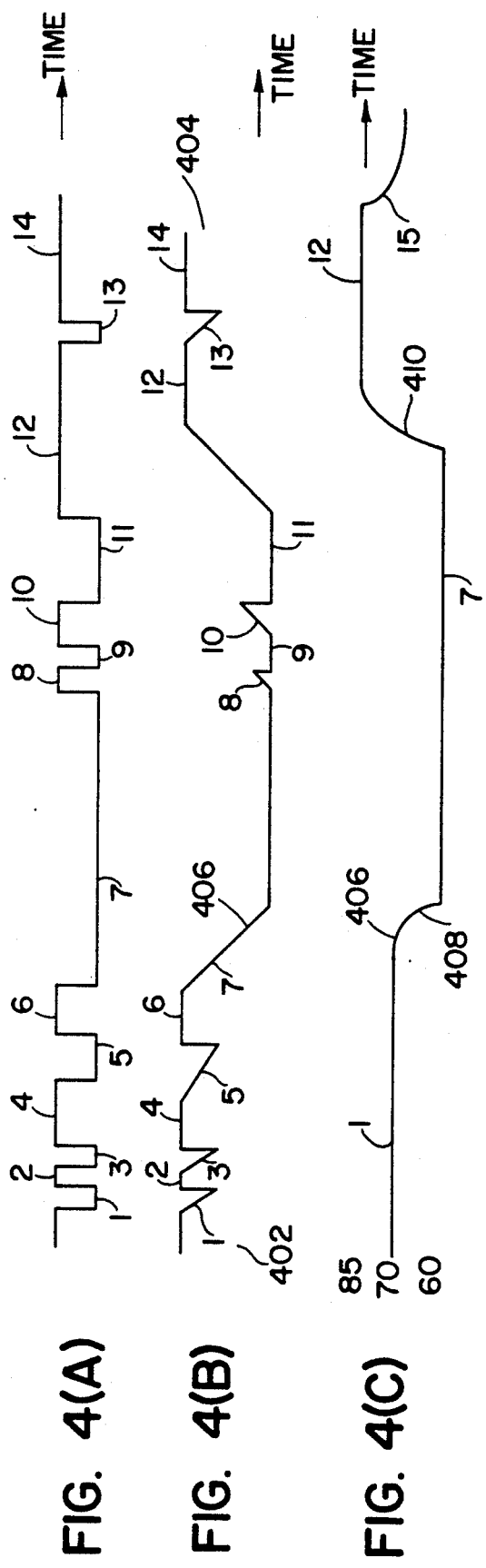

IMPLANTABLE MULTI-AXIS POSITION AND ACTIVITY SENSOR

BACKGROUND OF THE INVENTION

1. Field of the Invention

The present invention generally relates to implantable medical devices, and more particularly to a multi-axis, multi-purpose sensor for detecting the patient's posture and activity level. The sensor can be used in various medical devices such as cardiac pacemakers, defibrillators, neural stimulators, drug dispensing pumps and the like.

2. Description of the Art

Motion detectors have been known and used in various technologies including home intrusion alarms and theft detectors. One such motion detector is marketed by Universal Photonix under the tradename Mr. Outside, for use as a single axis vehicle theft sensor. The sensor is designed to discriminate a rocking motion caused by wind from a deliberate attempt to hoist a vehicle for towing it away.

Universal Photonix' detector is based on the bubble cell technology used in aircraft attitude detection. The detector includes a cylindrically shaped cell of about one centimeter in diameter which is approximately half filled with an electrically conductive liquid fluid. Two curved outer electrodes and a central electrode are partly immersed in the fluid.

A voltage is impressed across the two outer electrodes and the voltage drop between the central and the outer electrodes is measured. If the cell were level, the voltage drop would be equally divided between the outer electrodes and the central electrode. However, if the cell were tilted, the voltage drop would be less between the central electrode and the outer electrode which is more immersed in the electrolyte. The sensor is only a single axis sensor and therefore cannot detect attitude changes not aligned with its sensitive axis.

This type of detector has not been utilized in medical applications. More specifically, the sensor has not been used as a dual purpose activity sensor and posture detector in cardiac pacemakers.

Posture and activity sensors are known in the medical field. One conventional medical posture or sensor is described in a patent application Ser. No. 07/490,065 (now U.S. Pat. No. 5,031,618), filed on Mar. 7, 1990, which is entitled "Position-Responsive Neuro Stimulator", and which is assigned to Medtronic, Inc.

This position sensor can be located in a chronically implanted programmable spinal cord stimulator, and determines whether the patient is in an erect or supine position. Whenever the patient reclines, the position sensor notifies the implanted spinal cord stimulator to continue stimulation at different preprogrammed parameters. This sensor serves various neurological functions. However, it does not address activity and multi-directional posture sensing.

One exemplary medical position sensor is described in U.S. Pat. No. 4,846,195 to Alt. Alt describes an implantable position and motion sensor which detects the physical orientation of the implanted medical device within the body. The sensor also indicates the state of rest or activity movement of the patient, and includes a chamber, a mercury ball confined within the chamber, and several electrodes for establishing contact with the ball to signify the physical orientation of the medical device.

The Alt sensor relies on the use of a mercury ball for the establishment of electrical contact. The toxicity of mercury renders the Alt sensor undesirable for certain applications, in particular for permanently implantable medical devices. Also, the sensor does not accurately reflect patient posture since it is not a true two-axis device and has rudimentary position determination.

Wherefore, it would be highly desirable to have a posture sensor for use in implantable medical devices. The sensor should be of a small size and should provide multi-directional and accurate readings of the patient's physical position. The sensor should also indicate the state of rest or activity movement of the patient, and should not use toxic and potential harmful material such as mercury.

Various activity sensors are known and used in the medical field. The following patents generally exemplify the technology in the art: U.S. Pat. No. 4,428,378 to Anderson; U.S. Pat. No. 4,896,068 to Nilsson; U.S. Pat. No. 4,869,251 to Lekholm et al; and European Patent Application No. 383,732 to Inguaggiato.

The Anderson activity sensor is mounted within the pacemaker and detects the general activity level of the patient for altering the escape interval in response to the detected activity level. The Nilsson sensor utilizes flexural type piezoelectric elements to detect the activity level. The Lekholm sensor has a hollow member with a freely movable member therein which generates a mechanical vibration upon movement within the hollow member. The Inguaggiato sensor includes a mass of mercury which can assume a shape determined by the gravitational force and which is variable as a result of forces applied to the mass due to movement.

These conventional activity sensors do not satisfactorily resolve the concerns associated with the posture sensors, and the need still exists for a multi-axis, multi-purpose sensor for simultaneously detecting the patient's position and activity level.

BRIEF SUMMARY OF THE INVENTION

It is therefore an object of the present invention to address the above problems associated with conventional sensors, and to provide adequate solutions thereto.

Briefly, the above and further objects and features of the present invention are realized by providing a multi-axis, multi-purpose sensor for use with implantable medical devices such as cardiac pacemakers, defibrillators, neural stimulators, drug dispensing pumps, and the like, and for simultaneously detecting the patient's position and activity level. The sensor includes a hermetically sealed, fluid-tight, bio-compatible housing. The housing is formed of a plurality of adjacently secured sides. A plurality of side electrodes are coupled to the housing sides.

A central electrode is generally disposed at about the geometric center of symmetry of the housing, to allow measurement of impedances, voltages, or voltage changes between the central electrode and selected ones of the side electrodes. A non-toxic electrically conductive electrolyte fills about half the housing, and immerses part of the central electrode and the side electrodes.

In the preferred embodiment, the housing is configured in the shape of a cube having six sides, and the electrode includes six generally identical rectangularly shaped side electrodes. Each of these side electrodes is coupled to one side of the housing. The central electrode and the side electrodes are electrically accessible via feedthrough conductors through the housing.

The sensor further includes a low frequency bandpass filter for passing low frequency signals indicative of the patient's posture, and a high frequency bandpass filter for passing high frequency signals indicative of the patient's activity.

BRIEF DESCRIPTION OF THE DRAWINGS

The above and other objects and features of the present invention and the manner of attaining them, will become apparent, and the invention itself will be best understood, by reference to the following description and the accompanying drawings, wherein:

FIG. 3 is a block diagram illustration of a simplified circuit for a pacemaker according to the present invention, employing the sensor of FIGS. 1 and 2;

FIG. 3A is a circuit implementation of a multiplexor and analog to digital converter (ADC) showing sensor data generation for use in the pacemaker of FIG. 3; and FIGS. 4A–4C includes three graphs illustrating the response of the pacemaker of FIG. 3 to the sensor output.

DESCRIPTION OF THE PREFERRED EMBODIMENT

Figure 1:
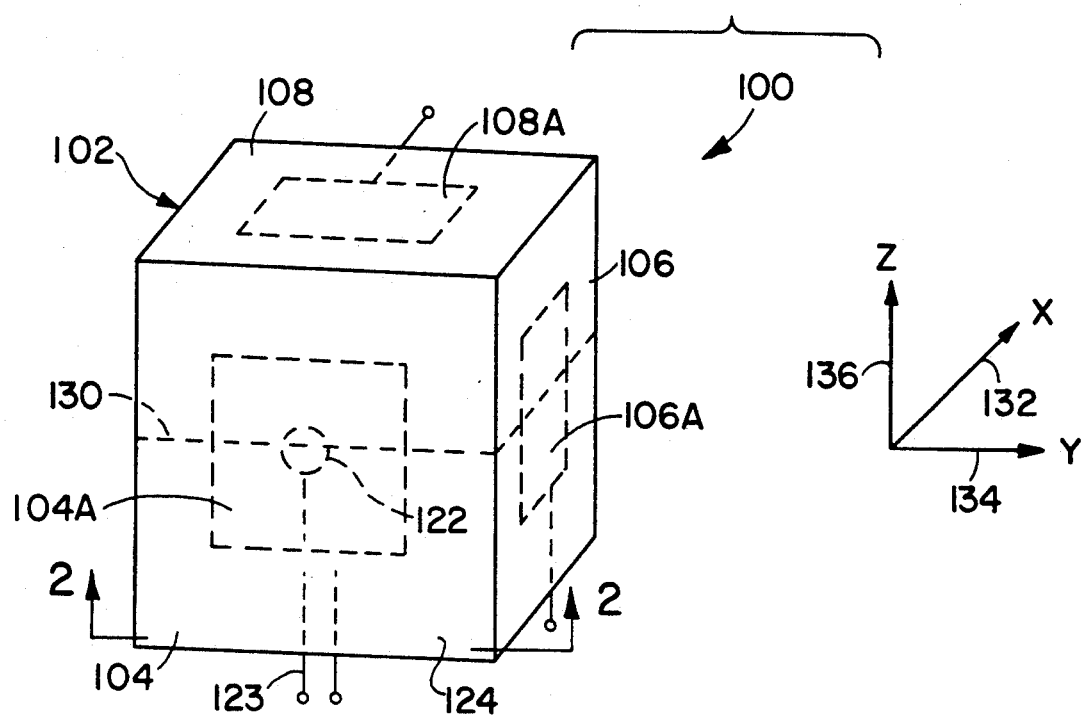
FIG. 1 is an isometric view of a sensor employed in the present invention, shown in a level position, and illustrating three side electrodes, one central electrode and the electrolyte in phantom lines.

Referring now to the drawings and more particularly to FIG. 1 thereof, there is illustrated a sensor 100 according to the present invention. The sensor 100 includes an outer enclosure 102 which is preferably configured in the shape of a cube, and which constitutes a hermetically sealed, fluid-tight housing. The enclosure 102 is composed of conventional structural biocompatible dielectric material, such as ceramic, phenolic resin, epoxy resin or polysulfone.

Figure 2:
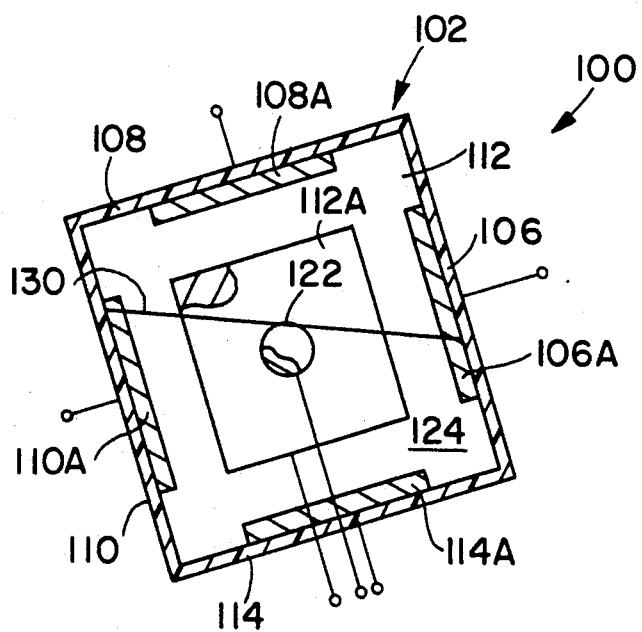
FIG. 2 is a cross-sectional side view of the sensor of FIG. 1 shown in a tilted position, and taken along line 2—2, with portions thereof being cut-away for clarity purposes.

The enclosure 102 includes six generally identical sides, three of which 104, 106 and 108 are illustrated in FIG. 1, and the remaining three sides 110, 112 and 114 are illustrated in FIG. 2. Six conductive plates 104A, 106A, 108A, 110A, 112A and 114A are used as side electrodes. Each of these plates is attached or coupled to one side of corresponding numeral reference, such that the center of symmetry of the enclosure 102 substantially corresponds to the center of symmetry of the electrodes 104A, 106A, 108A, 110A, 112A and 114A. As illustrated in FIG. 1, the electrode 104A is secured to the side 104, the electrode 106A is secured to the side 106, and the electrode 108A is secured to the side 108. Each of the six electrodes are electrically accessible from the outside of the sensor 100 via conventional feedthroughs.

A central electrically conductive electrode 122 accessible via a feedthrough 123, is generally disposed at the center of symmetry of the enclosure 102, to allow measurement of impedances, voltages and voltage changes between the central electrode 122 and the side electrodes 104A, 106A, 108A, 110A, 112A and 114A.

An electrolyte 124 is contained within the enclosure 102 and establishes electrical contact between the central electrode 122 and some of the side electrodes, depending on the position and inclination of the sensor 100. The sensor could be secured to the implanted medical device, or, in the alternative, it could be implanted independently, remotely from the implanted medical device. Yet another alternative would be to have the patient wear the sensor 100 externally, such that the output signals from the sensor 100 are transmitted by telemetry to the implanted medical device.

Referring now to FIG. 3, there is illustrated a simplified block circuit diagram for a pacemaker 300 employing the sensor 100. The signals at the output 302 of the sensor 100 are routed through a conventional multiplexor 314 and digitized by means of a conventional analog-to-digital converter 304, and are thereafter simultaneously passed through a low frequency bandpass filter 306 and a high frequency bandpass filter 308. The low frequency bandpass filter 306 gives an indication of the posture and inclination of the patient, whereas the high frequency bandpass filter 308 provides an indication of the patient's activity level.

The filtered signals at the output of the filters 306 and 308 are routed to a conventional activity based rate responsive pacemaker circuit including control logic circuitry 310, output/voltage multipliers 320 and 324, sense amplifiers 322 and 326, programming and data transmission circuit 326 and antenna 324, all of which control the pacing of the heart 312.

The activity based rate responsive pacemaker may be of the type described in a copending patent application entitled "METHOD AND APPARATUS FOR IMPLEMENTING ACTIVITY SENSING IN A PULSE GENERATOR", U.S. Ser. No. 07/455,717 (now U.S. Pat. No. 5,052,388), filed on Dec. 22, 1989, which is assigned to Medtronic, Inc. and which is incorporated herein by reference.

In operation, when the patient is in an upright position, the electrolyte 124 connects five side electrodes 104A, 106A, 110A, 112A and 114A to the central electrode 122. However, the voltages and impedances between the central electrode 122 and the side electrodes vary depending on the degree of immersion of the side electrodes in the electrolyte 124.

Hence, when the patient is in an upright position, the sensor 100 is level, and the side electrodes 104A, 106A, 110A, and 112A are substantially equally immersed in the electrolyte 124. Consequently, equal voltage and impedance values are measured between these side electrodes and the central electrode 122. The side electrode 114A, however, is totally immersed in the electrolyte 124, and hence the impedance measured between the central electrode 122 and the side electrode 108A is greater than the impedance between the central electrode 122 and the side electrode 114A.

If, as indicated in FIG. 2, the patient reclines to the front, the electrolyte surface 130 tends to remain in a horizontal position, thus causing the side electrode 110A to be more immersed in the electrolyte 124 than the opposite side electrode 106A. The two opposite side electrodes 104A and 112A remain equally immersed in the electrolyte 124.

If the angle of inclination is too steep, then the side electrode 110A would be completely immersed in the electrolyte 124, while the electrode 106A would be totally out of the electrolyte 124. Consequently, the impedance readings between the central electrode 122 and the six side electrodes are different, and a charting of the measured voltage or impedance values will permit an accurate determination of the patient's position and degree of inclination.

Conversely, if the patient reclines backward, the side electrode 106A will be more immersed in the electrolyte 124 than its opposite electrode 110A. However, the two opposite side electrodes 104A and 112A remain equally immersed in the electrolyte 124.

If, on the other hand, the patient is in a supine position, the electrode 110A will be completely immersed in the electrolyte 124, while the electrode 106A will be totally out of the electrolyte 124. The four side electrodes 108A, 112A, 114A and 104A will be equally immersed in the electrolyte 124.

As the patient starts to shift position to one side, such as the right side, the sensor 100 also tilts sidewise, and the side electrode 108A becomes more immersed in the electrolyte 124 than its opposite side electrode 114A. However, the two opposite side electrodes 104A and 112A will remain equally immersed in the electrolyte 124.

Therefore, the sensor 100 provides accurate readings of the patient's position, inclination and shifts in position. These readings are filtered by the low frequency bandpass filter 306 (FIG. 3) and fed to the position determining logic 316.

Additionally, the sensor 100 could be simultaneously used as an activity sensor for detecting the patient's activity level. When the patient's activity level rises, the electrolyte surface 130 tends to form high frequency ripples, which are measured and charted, as explained above in connection with the position sensing capability of the sensor 100. The ripples are converted into electrical signals which are filtered by the high frequency bandpass filter 308, and thereafter fed into an activity rate responsive pacemaker control logic circuit 310.

The control logic circuit 310 compares the output signals from the low frequency bandpass filter 306 and the high frequency bandpass filter 308, and determines the appropriate pacing rate of the pacemaker 300. In one embodiment, the logic circuit simply compares the output values from the activity responsive circuitry and the rate from the position sensitive circuit and selects the highest recommended pacing rate.

It is therefore clear that the present sensor presents considerable advantages and has a wide range of applications.

For example, the physiologic needs of a pacemaker patient at rest or sleep are greatly reduced from their awake and active mode. The position determining logic 316 and control logic 310 provide for the lower rate limit to be reduced to a more physiologic value during a sleep cycle—for example, 55 or 60 ppm. Upon rising, the pacing rate recovers to a more typical awake value—for example, 70 ppm. This invention allows more physiologic pacing, less emotional stress while at rest and circadian adjustment of the pacing rate.

Additionally, vasovagal syncope is a known cardiac dysfunction. Vasovagal syncope is often diagnosed after extensive clinical, electrophysiologic and neurological assessment via a head up tilt test, as described in the article entitled, "HEAD-UP TILT: A USEFUL TEST FOR INVESTIGATING UNEXPLAINED SYNCOPE", by Kenny et al, the Lancet, Jun. 14, 1986.

Symptoms include heart rate and blood pressure drop causing the syncopal episode. The position determining logic 316 and control logic 310 provide for an increase in pacing at an elevated rate (for example, 85 ppm or may be a programmable value) in the DDD or A-V sequential mode for a short period of time (for example, 5 minutes or may be a programmable time period) to artificially support the syncopal patient at an elevated pacing rate. Fallback pacing will then allow the patient's sinus rate or rate responsive pacing to overtake pacing control.

Additionally, tachycardia detection may be enhanced via the position determining logic 316 and control logic 310. If the sense amplifiers 322 and/or 326 are sensing at a high rate, the activity sensor filter 308 is showing low levels of activity and the position sensor logic 316 determines the patient is in the supine position, the control logic 310 may cause a pacing mode change or initiate a tachy therapy based on position.

Considering now the sensor 100 in greater detail with respect to FIG. 1, the enclosure 102 is preferably shaped as a cube. It should however be understood that the enclosure 102 could be configured as a cylinder, a sphere or similar other multi-sided shapes. The sensor should be as small as possible to allow incorporation into an implantable pacemaker, preferably 0.5 cm square, or less.

In the preferred embodiment, each of the electrodes 104A through 114A has a square shape, and is centered at about the geometric center of the corresponding side to which it is secured. It should however be understood that these electrodes can assume different shapes, such as a rectangle, a circle, a triangle, a parabola, or such other geometric shapes that will enable the mapping of the voltages, voltage changes, impedances and impedance changes between the central electrode 122 and various reference points on the side electrodes.

These side electrodes are composed of conventional conductive material such as stainless steel or titanium. The side electrodes may be supported remotely by feedthrough connector wires or may be connected to the side via an insulator.

The central electrode 122 is preferably composed of the same or similar conductive material as the side electrodes, and is generally spherically shaped. The central electrode is generally retained at about the geometric center of the enclosure 102 by conventional means such as an extended insulated feedthrough wire.

As illustrated in FIGS. 2 and 3, each of the side and central electrodes is connected, via a corresponding conductor to a multiplexor circuit 314, where the voltages and impedances across the central and the side electrodes, as well as between the side electrodes, are monitored and fed to the analog-to-digital converter 304 for measurement and subsequent analysis.

The signals from the multiplexor circuit 314 are sampled by the analog-to digital converter 304 at 50 samples per second for each of the three-axis sampled. Additionally, the sample time may be on the order of 30 micro seconds, thereby consuming little additional power from the power source 318.

The low frequency bypass filter 306 passes only those signals from 0.2 to 1 Hz. This frequency range is indicative of the patient's posture or position shift. The high frequency bandpass filter 308 passes only those signals between 3 and 25 Hz. This frequency range is indicative of the patient's activity level.

The position determining logic 316 analyses the output signal from the filter 306 and determines the patient's positional orientation via comparing programmed or initialized data with measured data. For example, with the patient in an upright position and with the sensor oriented with electrode set 108A and 114A in a vertical orientation, the impedance between the center electrode 122 and side electrode 108A should be very high (>100k ohm) while the impedance between the center electrode 122 and side electrode 114A should be about 500-1000 ohm. This condition plus the other axis electrodes, 110A/106A, having similar low values indicates an upright position.

Referring now to the graphs in FIG. 4, they include three graphs illustrating the response of the pacemaker 300 to the low frequency bandpass filter 306. Graph (A) illustrates a series of signals at the output of the position determining logic 316. Graph (B) illustrates a series of signals at the output of the filter 306, and corresponding to the signals in Graph (A). Graph (C) illustrates the signals at the output of the atrial and ventricular output/voltage multipliers, 320 and 324, and corresponding to the signals in Graphs (A) and (B).

The signal shown in Graph (A) is representative of the vertical axis (X axis, 132 in FIG. 1) determining portion of the sensor 100. The other two axis would generate similar outputs representative of postural changes relative to the Y axis (134) and Z axis (136), respectively. In the preferred embodiment, the pacemaker is programmed and initialized upon implant, automatically determining the X, Y and Z axes orientation based upon pacemaker placement and orientation in the patient. The sensor axes are sampled cyclically at 50 samples per second, via the multiplexor 314 and as shown in FIG. 3A.

FIG. 3A shows the sampling of one axis and functions as follows. Closing the CMOS switches 350 and 352 provides a current path from the battery 318 through plate 106A, the conductive liquid 124 between the electrodes 106A and 122, the electrode 122, the conductive liquid 124 between the electrodes 122 and 110A and the plate 110A to the battery ground. When switch 354 is closed, it allows the ADC 304 to sample and convert the voltage from the electrode 106A to the ground (voltage sample 1, VS1).

When switch 354 is opened and the switch 356 is closed, the ADC 304 samples and converts the voltage from the electrode 122 to ground (voltage sample 2, VS2). After this second conversion, all the switches 350, 352, 354 and 356 are opened. The impedance ratio between the center electrode 122 and the two side electrodes 106A and 110A may be calculated by:

$$V106A = (VS1 - VS2);$$

$$V110A = (VS2).$$

The above described three-axis function overcomes prior art failures by being able to differentiate false alarm conditions, such as the patient bending over or rotation about the spinal axis while lying down, as in rolling over while lying down.

In Graph (A) of FIG. 4, the upper lines, such as the even numbered lines 2, 4, 6 and 8 indicate that the patient is an upright position, while the lower lines, such as the odd numbered lines 1, 3, 5 and 7 indicate that the patient is in a supine position.

The signals illustrated by lines 1 through 6 in FIG. 1 are filtered by the filter 306 and are illustrated in Graph (B) by lines of corresponding numeral references. The filtering may alternately be done in the position determining logic 316 via a retriggerable one-shot that must reach a predetermined value to indicate a position change.

However, these filtered signals are deemed to be artifacts generated by minor position changes, since they do not reach a lower threshold level 402. Consequently, as illustrated in Graph (C), the logic circuit 310 ignores these signals and assumes that the patient is in an upright position, and produces a pacing rate commensurate with such upright position, 70 ppm, as illustrated by the straight line 1 in Graph (C). In accordance with this invention, the rate may be at the lower rate or alternatively an activity controlled rate up to the upper rate limit.

Considering now line 7 in Graph (A), it extends for a relatively long period of time and reaches a threshold at 406. The logic circuit 310 then determines that the patient has now moved to a supine position, and changes the pacing rate accordingly. It should be noted that, as soon as the threshold level has been reached at point 406, the pacing rate is changed gradually along a decay curve 408 having a time constant of about 15 seconds, as illustrated in Graph (C). Line 7 in Graph (C) allows the pacing rate to be reduced to the lower rate limit or alternatively to the hyperesis rate to allow the patient the ability to rest or sleep in a physiologic manner.

The signals illustrated by lines 8 through 10 in Graph (A) are determined to be artifacts, since the corresponding signals in Graph (B) do not reach an upper threshold level 404. Consequently, these signals are ignored by the control logic circuit 310, as illustrated by the continuous line 7 in Graph (C).

Line 12 in Graph (A) represents a change in the patient's position from a supine to an upright position, since, as illustrated by line 12 in Graph (B), the upper threshold level 404 has been reached. Consequently, the control logic circuit 310 changes the pacing rate accordingly. The pacing rate is not changed abruptly, however, to prevent patient discomfort, but is rather gradually changed along an attack curve 410 having a time constant of about 15 seconds, and pacing at an elevated rate (as an example, 85 ppm) as illustrated in Graph (C). After pacing at an elevated rate for a period of time (as an example, 5 minutes), the pacing rate decays to the activity responsive rate or the lower rate along line 15.

While particular embodiments of the present invention have been disclosed, it is to be understood that various different modifications are possible and are contemplated within the scope of the specification, drawings, abstract and appended claims.

What is claimed is:

1. An implantable cardiac pacemaker comprising a multi-axis sensor for measuring the patient's activity level and for giving indications of the patient's posture, said sensor including:
   a. hermetically sealed, fluid-tight, bio-compatible housing;
   b. said housing being formed of a plurality of adjacently secured sides;
   c. a plurality of side electrodes being coupled to said sides;
   d. a central electrode generally disposed at about the center of said housing to allow measurement of impedances, voltages, or voltage changes between said central electrode and selected ones of said side electrodes; and
   e. electrically conductive electrolyte filling a portion of said housing.

2. A sensor for detecting the onset of tachycardia comprising:
   a. first means for detecting whether the patient is in a generally supine position;
   b. second means for detecting whether the patient's activity level is below a predetermined minimum value;
   c. third means for detecting cardiac intrinsic activities above a predetermined maximum value; and
   d. means for diagnosing the onset of tachycardia when said first detecting means indicates that the patient is in a generally supine position, when said second detecting means indicates that the patient's activity level is below said minimum value, and when said third detecting means indicates that the cardiac intrinsic activities are above said maximum value.

3. The sensor as defined in claim 2 further including means for a staged therapy for ending said tachycardia.

4. The sensor as defined in claim 3 wherein said staged therapy includes means for cardiac pacing for ending said tachycardia.

5. The sensor as defined in claim 4 wherein said staged therapy further includes means for cardioverting the heart for ending said tachycardia.

6. The sensor as defined in claim 5 wherein said staged therapy further includes means for defibrillating the heart for ending said tachycardia.

7. A method for detecting the onset of tachycardia comprising the steps of:
   a. detecting whether the patient is in a supine position;
   b. detecting whether the patient's activity level is below a predetermined minimum value;
   c. detecting cardiac intrinsic activities above a predetermined maximum value; and
   d. diagnosing the onset of tachycardia when the patient is in a generally supine position, when the patient's activity level is detected to be below said minimum value, and when the cardiac intrinsic activities are detected to be above said maximum value.

8. The method of defining claim 7 further including the step of ending said tachycardia.

9. The method as defined in claim 8 wherein said step of ending said tachycardia includes the step of inducing a staged therapy.

10. The method as defined in claim 9 wherein said step of inducing said staged therapy includes cardiac pacing, cardioversion and defibrillation.

* * * * *